United States Patent [19]

Chin

[11] Patent Number: 5,256,561
[45] Date of Patent: Oct. 26, 1993

[54] MONOCLONAL ANTIBODY TO HIV-2 AND USES THEREOF

[75] Inventor: Jade Chin, Edison, N.J.

[73] Assignee: Abbott Laboratories, Abbott Park, Ill.

[21] Appl. No.: 811,592

[22] Filed: Dec. 20, 1991

[51] Int. Cl.[5] .......................... C07K 15/28; C12N 5/20
[52] U.S. Cl. .......................... 435/240.27; 530/388.35; 530/387.1; 530/388.1; 530/388.2; 530/388.3; 435/5; 435/974; 935/104; 935/89; 935/95; 935/102
[58] Field of Search .................. 530/387; 935/104; 435/240.27

[56] References Cited

FOREIGN PATENT DOCUMENTS 2007567  7/1990  Canada .

OTHER PUBLICATIONS

Hunt et al., "Discrimination Between HIV1 and HIV 2 Seropasline Individuals Using Mouse Monoclonal Antibodies Directed to HIV Transembrane Proteins" AIDS Res Hiv Ret. 687, 1990, pp. 883-898.

Komatsu et al. "Production and Characterization of Mouse Monclonal Antibodies Against the Thransmembrane Protein of Human Immuno deficiency Virus Type 2" AIDS Resaflum Ret. 7(12) Dec. 1991, pp. 999-1005.

Primary Examiner—Christine M. Nucker
Assistant Examiner—Chris Dubrule
Attorney, Agent, or Firm—Priscilla E. Porembski; Daniel R. Curry

[57] ABSTRACT

A monoclonal antibody which specifically binds to HIV-2 gp36 antigen and does not specifically bind to HIV-1 antigens. The monoclonal antibody is useful in immunoassays as a capture reagent, as part of an indicator reagent, and/or as a positive control.

2 Claims, 6 Drawing Sheets

| CKS | | p41 |
|---|---|---|
| 239 | 18 | 108  10 | rp41 HIV-2 Rod

MONOCLONAL ANTIBODY TO HIV-2 AND USES THEREOF

BACKGROUND OF THE INVENTION

This invention relates generally to monoclonal antibodies, and more particularly, relates to a murine monoclonal antibody which specifically binds to HIV-2 and does not significantly bind to HIV-1, uses for the monoclonal antibody, and kits which contain the monoclonal antibody.

Present epidemiological data suggest that the Acquired Immunodeficiency Syndrome (AIDS) is caused by at least two types of human immunodeficiency viruses, collectively designated as HIV. Human immunodeficiency virus type 1 (HIV-1) has been isolated from patients with AIDS and AIDS-related complex (ARC), and from healthy persons at high risk for AIDS. See, for example, F. Barre-Sinoussi et al., Isolation of T-Lymphotropic Retrovirus From a Patient At Risk For Acquired Immune Deficiency Syndrome (AIDS), *Science* 220:868-871 (1983); M. Popovic et al., Detection, Isolation and Continuous Production Of Cytopathic Retroviruses (HTLV-III) From Patients With AIDS are Pre-AIDS, *Science* 224:497-500 (1984); and R. C. Gallo et al., Frequent Detection and Isolation Of Cytopathic Retroviruses (HTLV-III) From Patients With AIDS and At Risk For AIDS, *Science* 224:500-503 (1984).

HIV-1 reportedly is transmitted by sexual contact, exposure to blood or certain blood products, or from an infected mother to her fetus or child. P. Piot et al., AIDS: An International Perspective, *Science* 239:573-579 (1988). Also, the incidence of HIV-1 antibodies is high in AIDS and ARC patients and persons at risk. M. G. Sarngadharan et al., Antibodies Reactive With Human T-Lymphotrophic Retroviruses (HTLV-III) In The Serum of Patients With AIDS, *Science* 224:506-508 (1984). This virus can be isolated from nearly 90% of all seropositive individuals. D. Gallo et al., Comparative Studies On Use Of Fresh and Frozen Peripheral Blood Lymphocyte Specimens For Isolation Of Human Immunodeficiency Virus and Effects Of Cell Lysis On Isolation Efficiency, *J. Clin. Microbiology* 25:1291-1294 (1987).

A second HIV virus, designated as Human Immunodeficiency Virus Type 2 (HIV-2), was isolated from patients with AIDS in West Africa in 1986. F. Clavel et al., Isolation Of a New Human Retrovirus From West African Patients With AIDS, *Science* 233:343-346 (1996). HIV-2 infections now have been identified in humans outside of the initial endemic area, and have been reported in Europeans who have lived in West Africa or those who have had sexual relations with individuals from this region, homosexuals with sexual partners from the endemic area, and others. See, for example, A. G. Saimot et al., HIV-2/LAV-2 In Portuguese Man With AIDS Who Had Served In Angola In 1968-74, *Lancet* i:686 (1987); M. A. Rey et al., HIV-1 and HIV-2 Double Infection In French Homosexual Male With AIDS-Related Complex, *Lancet* i:3-88-389 (1987); A. Werner et al., HIV-2, *Lancet* i:8-68-869 (1987); G. Brucker et al., HIV-2 infection In Two Homosexual Men In France, *Lancet* i:223 (1987); K. Marquart et al., HIV-2 in West Germany, *AIDS* 2:141 (1988); CDC, AIDS due to HIV-2 infection, MMWR 37:33-35 (1987); Anon., HIV-2 Detected In UK, *Nature* 332:295 (1988).

Retrospectively-diagnosed cases of AIDS due to HIV-2 infection, acquired in the late 1960's, have been reported in France and the United Kingdom, and the first examples of transfusion associated HIV-2 infection recently have been documented. N. Burin des Roziers, Infection Par Le Virus HIV-2 Avec Longue Period D'incubation, *Presse Med* 16:1981 (1987); A. Bryceson et al., HIV-2 Associated AIDS In The 1970's, *Lancet* ii:221 (1988); and A. M. Courouce et al., A Prospective Study of HIV-2 Prevalence In France, *AIDS* 2:261-265 (1988).

The differentiation of HIV-2 from HIV-1 is based on the following factors: (1) HIV-1 DNA probes constructed with the entire genome fail to hybridize with HIV-2 RNA under medium or high stringency conditions; (2) there is less than 60% amino acid identity (HOMOLOGY) for the gag and pol gene products, and only 37% for env encoded proteins between the two viruses; and (3) HIV-1 antibody containing sera have no neutralizing effect on HIV-2 isolates, contrasting with the cross-neutralization activity of HIV-2 antisera on HIV-1 strains. F. Clavel, HIV-2, The West African AIDS Virus, *AIDS* 1:135-140 (1987); R. A. Weiss et al., HIV-2 Antisera Cross-Neutralize HIV-1, *AIDS* 2:95-100 (1988). Serologic studies indicate that while HIV-1 and HIV-2 share multiple common epitopes in their core antigens, the envelope glycoproteins of these two viruses are much less cross-reactive. F. Clavel, supra. This limited cross-reactivity of the envelope antigens is believed to explain why currently available serologic assays for HIV-1 may fail to react with certain sera from individuals with antibody to HIV-2. F. Denis et al., Comparison Of 10 Enzyme Immunoassays For Detection Of Antibody To HumanImmunodeficiency Virus Type 2 In West African sera, *J. Clin. Micro* 26:1000-1004 (1988). Recently issued U.S. Pat. No. 5,055,391 maps the HIV-2 genome and provides assays to detect the virus.

Tests developed for detection of HIV-1, HIV-2, or both, thus must contain reagents which are useful for determining the specific presence of either or both of the viruses in a test sample. The need therefore exists for reagents, such as monoclonal antibodies, capable of reacting only with HIV-2 from human sources, which antibody does not cross-react with HIV-1 antigenic determinants.

SUMMARY OF THE INVENTION

This invention provides a monoclonal antibody which specifically binds to HIV-2 gp36 antigen in human test samples, and does not significantly bind to HIV-1antigens in human test samples. This monoclonal antibody, termed 7-1054-180, is secreted by the hybridoma cell line 7-1054-180. The hybridoma cell line 7-1054-180 has been deposited at the American Type Culture Collection, 12301 Parklawn Drive, Rockville, Md. 20852, as of Nov. 1, 1991, under A.T.C.C. deposit No. HB 10908.

The invention provides an improvement in known immunoassays which detect HIV-1 and/or HIV-2, by adding a known amount of monoclonal antibody which specifically binds to HIV-2 gp36 antigen and does not significantly bind to HIV-1 antigens. In this circumstance, the monoclonal antibody is useful as a positive control to specifically detect HIV-2 gp36 antigen, in an assay which can detect either or both HIV-1 and HIV-2.

Test kits which contain monoclonal antibody 7-1054-180 secreted by the cell line 7-1054-180 in a separate vial or container also are provided.

DETAILED DESCRIPTION OF THE INVENTION

The monoclonal antibody of the present invention can be employed in various assay systems to determine the presence, if any, of HIV-2 in a test sample. Fragments of the monoclonal antibody provided also may be used. For example, in a first assay format, a polyclonal or monoclonal anti-HIV-2 antibody or a fragment thereof, which has been coated on a solid phase, is contacted with a test sample which may contain HIV-2 antigens, to form a mixture. This mixture is incubated for a time and under conditions sufficient to form antigen/antibody complexes. Then, an indicator reagent comprising a monoclonal or a polyclonal antibody or a fragment thereof, which specifically binds to HIV-2 antigen, to which a signal generating compound has been attached, is contacted with the antigen/antibody complexes to form a second mixture. This second mixture then is incubated for a time and under conditions sufficient to form antibody/antigen/antibody complexes. The presence of HIV-2 antigen present in the test sample and captured on the solid phase, if any, is determined by detecting the measurable signal generated by the signal generating compound. The amount of HIV-2 antigen present in the test sample is proportional to the signal generated.

Alternatively, a polyclonal or monoclonal anti-HIV-2 antibody or fragment thereof which is bound to a solid support, the test sample and an indicator reagent comprising a monoclonal or polyclonal antibody or fragments thereof, which specifically binds to HIV-2 antigen to which a signal generating compound is attached, are contacted to form a mixture. This mixture is incubated for a time and under conditions sufficient to form antibody/antigen/antibody complexes. The presence, if any, of HIV-2 antigen present in the test sample and captured on the solid phase is determined by detecting the measurable signal generated by the signal generating compound. The amount of HIV-2 antigen present in the test sample is proportional to the signal generated. In this or the assay format described above, the monoclonal antibody of the invention can be employed either as the capture phase or as part of the indicator reagent.

In another alternate assay format, the monoclonal antibody of the invention can be employed as a competitive probe for the detection of antibodies to HIV-2 antigen. For example, HIV-2 antigens, preferably HIV-2 envelope antigens, coated on a solid phase, are contacted with a test sample suspected of containing antibody to HIV-2, and incubated with an indicator reagent comprising a signal generating compound and the monoclonal antibody of the invention for a time and under conditions sufficient to form antigen/antibody complexes of either the test sample and indicator reagent to the solid phase or the indicator reagent to the solid phase. The reduction in binding of the monoclonal antibody of the invention to the solid phase, as evidenced by a reduction in the generated signal, can be quantitatively measured. A measurable reduction in the signal compared to the signal generated from a confirmed negative HIV-2 test sample would indicate the presence of anti-HIV-2 antibody in the test sample.

In yet another detection method, the monoclonal antibody of the present invention can be employed in the detection of HIV-2 antigen in fixed tissue sections, as well as fixed cells by immunohistochemical analysis, by standard methods well-known to those skilled in the art.

In addition, these monoclonal antibodies can be bound to matrices similar to CNBr-activated sepharose and used for the affinity purification of specific HIV-2 antigens from cell cultures, or biological tissues such as blood and liver.

The monoclonal antibody of the invention also can be used for the generation of chimeric antibodies for therapeutic use, or other similar applications.

The monoclonal antibodies or fragments thereof can be provided individually to detect HIV-2 antigen. Combinations of the monoclonal antibody (and fragments thereof) of the present invention provided herein also may be used in combination with other monoclonal antibodies that have differing specificities for HIV-2 as components in a mixture or "cocktail" of HIV-2 antibodies, each having different binding specificities. Thus, this cocktail can include the monoclonal antibody of the invention directed to a specific antigenic determinant of p36 of the HIV-2 genome, along with different monoclonal antibodies directed to other HIV-2 antigenic determinants. This cocktail of monoclonal antibodies would be used in place of the single monoclonal antibody as described in the assay formats herein.

The polyclonal antibody or fragment thereof which can be used in the assay formats should specifically bind to HIV-2 antigen. The polyclonal antibody used preferably is of mamallian origin; human, goat, rabbit or sheep anti-HIV-2 polyclonal antibody can be used. Most preferably, the polyclonal antibody is rabbit polyclonal anti-HIV-2 antibody. The polyclonal antibodies used in the assays can be used either alone or as a cocktail of polyclonal antibodies. Since the cocktails used in the assay formats are comprised of either monoclonal antibodies or polyclonal antibodies having different HIV-2 specificity, they would be useful for diagnosis, evaluation and prognosis of HIV-2 infection, as well as for studying HIV-2 protein differentiation and specificity.

The monoclonal antibody also can be used in a cocktail of monoclonal antibodies when detecting the combined presence of either or both HIV-1 and HIV-2. In this type of assay format, different HIV-1 and HIV-2 antibodies are immobilized on solid supports. A test sample is contacted with the antibody-immobilized solid supports, incubated for a time and under sufficient to form antigen/antibody complexes, and then contacted with either a cocktail of polyclonal or monoclonal antibodies specific to the antigens to which a signal generating compound (label) has been attached, and incubated for a time and under conditions sufficient to form antibody/antibody/antigen complexes. The presence of either or both of the antibodies is determined by detecting the measurable signal generated by the label.

Test samples which can be tested by the methods of the present invention described herein include human and animal body fluids such as whole blood, serum, plasma, cerebrospinal fluid, urine, biological fluids such as cell culture supernatants, fixed tissue specimens and fixed cell specimens.

The "solid phase" is not critical and can be selected by one skilled in the art. Thus, latex particles, microparticles, magnetic or non-magnetic beads, membranes, plastic tubes, walls of microtiter wells, glass or silicon chips and tanned sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-megnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates. copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable.

It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces.

The indicator reagent comprises a signal generating compound (label) which is capable of generating a measurable signal detectable by external means conjugated (attached) to a specific binding member for HIV-2. "Specific binding member" as used herein means a member of a specific binding pair. That is, two different molecules where one of the molecules through chemical or physical means specifically binds to the second molecule. In addition to being an antibody member of a specific binding pair for HIV-2, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HIV-2 as in a sandwich assay, to the capture reagent as in a competitive assay, or to the ancillary specific binding member as in an indirect assay.

The various signal generating compounds (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

Other embodiments which utilize various other solid phases also are contemplated and are within the scope of this invention. For example, ion capture procedures for immobilizing an immobilizable reaction complex with a negatively charged polymer, described in copending U.S. Patent. application Ser. No. 150,278 corresponding to EP publication 0326100, and U.S. patent application Ser. No. 375,029 (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in copending U.S. patent application Ser. No. 921,979 corresponding to EPO Publication No. 0 273,115, which enjoys common ownership and which is incorporated herein by reference.

Also, the methods of the present invention can be adapted for use in systems which utilize microparticle technology including in automated and semi-automated systems wherein the solid phase comprises a microparticle. Such systems include those described in pending U.S. patent applications Ser. Nos. 425,651 and 425,643, which correspond to published EPO applications Nos. EP 0 425 633 and EP 0 424 634, respectively, which are incorporated herein by reference.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercaptopropyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio] propionate), SMCC (succinimidyl-4-[N-maleimidomethyl] cyclohexane-1-carboxylate), SIAB (succinimidyl [4-iodoacetyl] aminobenzoate), and SMPB (succinimidyl 4-[1-maleimidophenyl] butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. Patent applications Ser. No. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the peptides of the present invention can be utilized in non-solid phase assay systems. These assay systems are known to those skilled in the art, and are considered to be within the scope of the present invention.

The monoclonal antibody of the invention can be used as a positive control in an assay which is designed to detect the presence of at least HIV-2 antibody, or in an assay that differentiates HIV-1 from HIV-2 infection. In an assay which detected the presence of HIV-2 antibody in a test sample, HIV-2 antigens would be used as a capture phase. These HIV-2 antigens could be prepared by various purification means to obtain viral lysates, synthetic peptides of various immunogenic regions of the HIV-2 genome, and/or recombinant proteins produced by using either synthetic or native antigens or epitopes of antigens. It also is contemplated that these types of HIV-2 antigens could be employed in a variety of assay formats including those described herein as either the capture phase or detection phase. The use of the monoclonal antibody of the invention would ensure that the reagents provided to detect HIV-2 antibody were performing adequately by being used in place of a test serum in the performance of the assay, according to procedures known to those of ordinary skill in the art. The monoclonal antibody of the invention also is useful as a positive control in tests which detect HIV-1 and/Or HIV-2, or which can differentiate HIV-1 from HIV-2. In these types of assays, when results are generated to reactivity of a test sample to various antigenic determinants of HIV-1 and/or HIV-2, it is important to ensure that the antigen used in the test is performing as expected. This quality assurance would be performed by substituting the monoclonal antibody of the invention for the test sample, performing an assay which contacts a test sample with a solid phase to which HIV-1 and HIV-2 proteins have been attached and incubating for a time and under conditions sufficient for antigen/antibody complexes to form, then contacting the so-formed complexes with antibodies specific for HIV-1 and HIV-2, and determining the result of the assay according to pre-determined parameters. Results of the assay performed by using the monoclonal antibody of the invention as described which are outside the pre-determined parameters would render the assay results questionable or void.

It is contemplated that the reagent employed for the assay can be provided in the form of a kit with one or more containers such as vials or bottles, with each container containing a separate reagent such as a monoclonal antibody, or a cocktail of monoclonal antibodies, employed in the assay. These kits also could contain vials or containers of other reagents needed for performing the assay, such as washing, processing and indicator reagents.

The following examples demonstrate the advantages and utility of the 7-1054-180 monoclonal antibody of the invention by describing methods for the development, characterization, epitope mapping and clinical utility of this monoclonal antibodies. The methods used for monoclonal antibody development follow procedures known in the art and detailed in Kohler and Milstein, *Nature* 256:494 (1975), and reviewed in J. G. R. Hurrel, ed., *Monoclonal Hybridoma Antibodies: Techniques and Applications*, CRC Press, Inc., Boco Raton, FL (1982). Another method of monoclonal antibody development which is based on the Kohler and Milstein method is that of L. T. Mimms et al., *Virology* 176:604–619 (1990), which is incorporated herein by reference. These examples are meant to illustrate, but not to limit, the spirit and scope of the invention.

EXAMPLES

EXAMPLE 1

Preparation and Maintenance of Myeloma Cell Line

A recombinant DNA clone was constructed to contain the amino terminal 108 amino acids of the Rod isolate of HIV-2 gp41 (Guyader et al., *Nature* 326:662–669 [1987]) as a fusion protein with CKS. This antigen (designated rp41 HIV-2 Rod) was used to immunize a mouse from which an immune splenocyte was fused to a SP2/0-Ag14 myeloma cell to produce a hybridoma cell line (7-1054-180) that secretes a monoclonal antibody of immunoglobulin (Ig) class G (IgG) monoclonal antibody reactive with HIV-2 gp41. The resultant IgG was produced in mouse ascites fluid and was purified by Protein A affinity chromatography.

A. Construction and Expression of Recombinant Immunogen.

Figure 1:
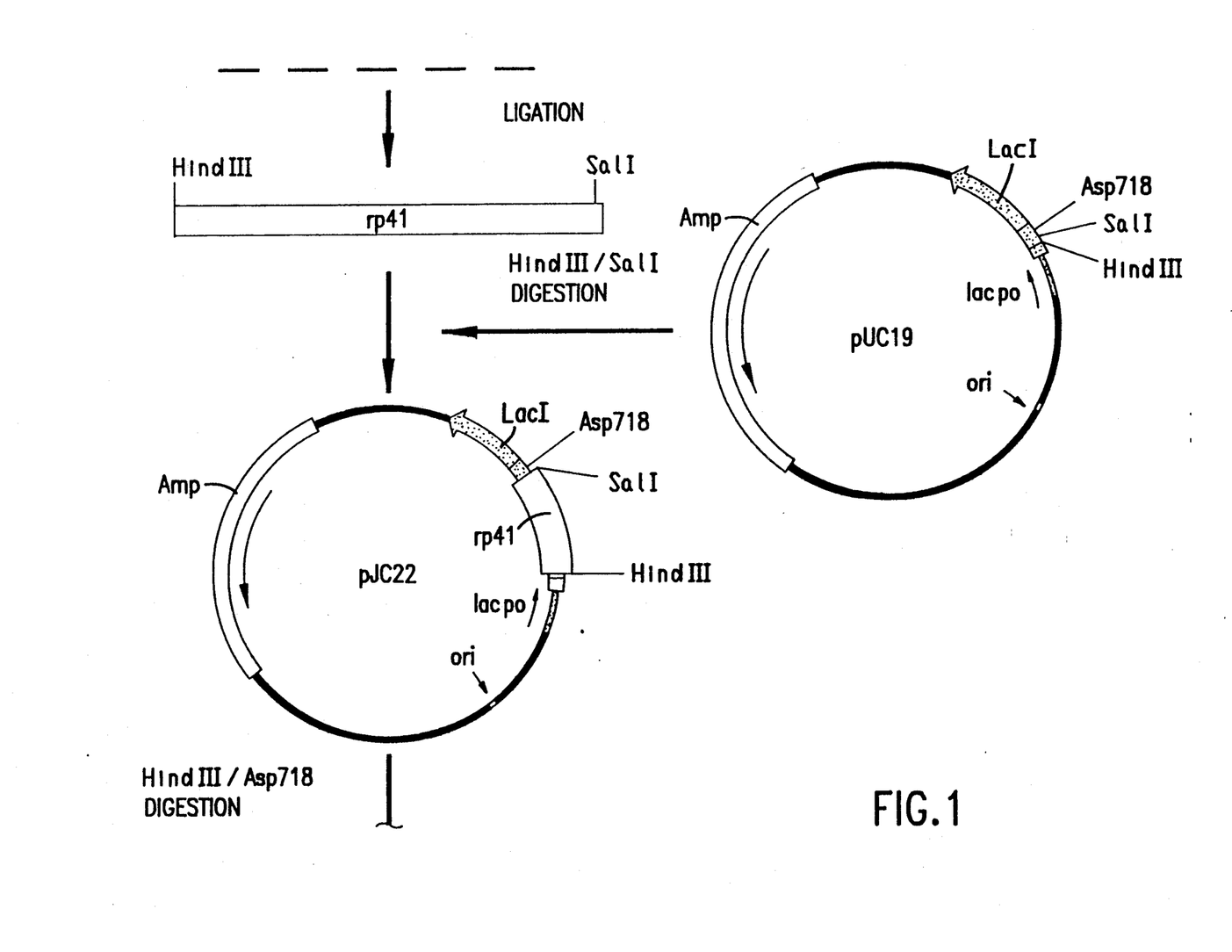
FIG. 1 is a schematic diagram of the construction of plasmid pJC100/XL-1.
Figure 1A:
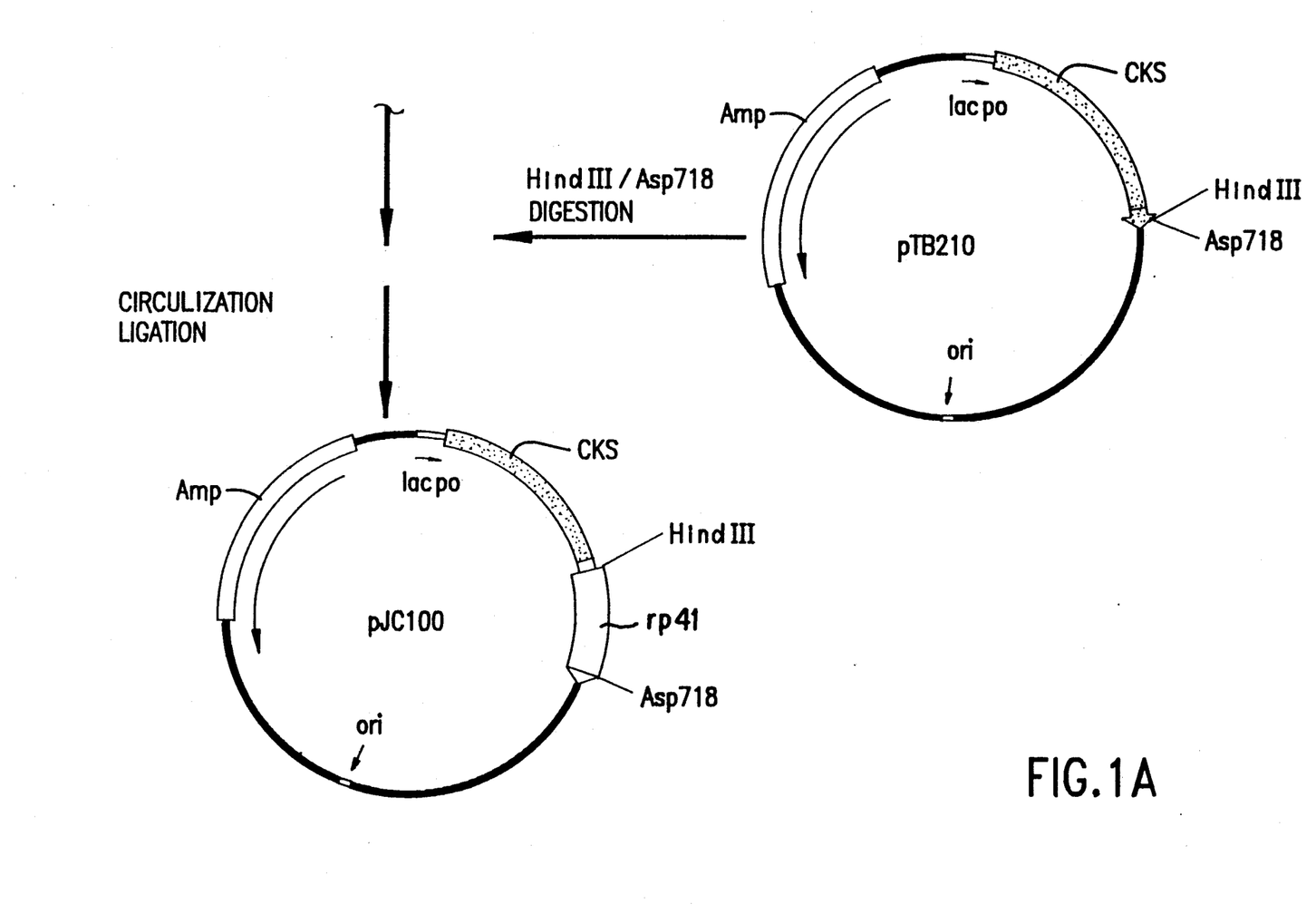

FIG. 1 is a schematic diagram of the construction of plasmid pJC100/XL-1. This plasmid is the subject matter of patent application U.S. Ser. No. 275,309 (EP Publication 0370458) which enjoys common ownership and is incorporated herein by reference. The construction of the recombinant *E. coli* clone expressing the rp41 HIV-2 Rod antigen was performed in three stages. First, five individual oligonucleotides were synthesized and cloned separately. Second, the five sequences were assembled and ligated into a cloning vector. Third, the rp41 HIV-2 Rod sequences were subcloned into a CKS expression vector.

Thus, a DNA fragment coding for 108 amino acids (502 through 609) of the envelope gene of HIV-2 was chemically synthesized utilizing codons optimized for expression in *E. coli*. Five individual oligonucleotides were synthesized and cloned separately by the process of oligonucleotide directed double-strand break repair. The sequences were confirmed by the well-known Sanger dideoxy method (F. Sanger et al., *J. Molec. Biol* 162:729 (1982). The genes were assembled and ligated into the cloning vector pUC19 and a HindIII-SalI fragment. The resulting plasmid was named pJC22.

The expression vector pTB210 allowed the fusion of recombinant genes to the CKS protein. Plamid pTB210 is disclosed in U.S. patent application Ser. No. 276,263, which is a continuation-in-part application of U.S. Ser. No. 167,067, both of which enjoy common ownership and are incorporated herein by reference. This plasmid consisted of the plasmid pBR322 with a modified lac promotor fused to a kdsB gene fragment. This fragment encoded the first 239 of the entire 248 amino acids of the CKS gene and a synthetic linker fused to the end of the kdsB fragment. The synthetic linker included multiple restriction sites for insertion of genes, translational stop signals and the transcriptional terminator.

Plasmid pJC22 was digested with HindIII and Asp718, and a 360 base pair fragment encoding the rp41 HIV-2 Rod was isolated and inserted into the HindIII and Asp718 site of the expression vector pTB210. The resulting plasmid, designated pJC100, expressed the envelope region as a fusion with the CKS protein. The expression of the fusion protein was under the control of the lac promoter.

Figure 2:
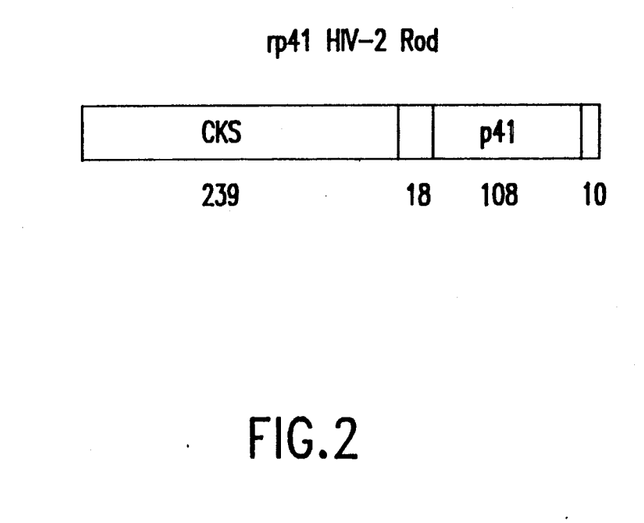
FIG. 2 illustrates schematically the recombinant protein encoded by plasmid pJC100.

The promoter region, transcriptional start and ribosomal binding site spanned bases 1–125. The coding region was comprised of sequence derived from the 239 amino acids of the CKS protein (bases 126–842) and the 18 amino acids from the synthetic polylinker (bases 843–896). This was followed by 108 residues of the amino end of the HIV-2 envelope (bases 897–1220) and 10 amino acids of the remainder of the polylinker (bases 1221–1250). Translation was terminated at the termination codon at bases 1251–1253. The recombinant protein encoded by plasmid pJC100 is illustrated schematically in FIG. 2. The amino terminus consists of 239 amino acids of CKS followed by 18 non-HIV amino acids, 108 amino acids of HIV-2 p41 Rod abd 10 non-HIV amino acids.

In summary, the plasmid pJC100 encoded the recombinant protein rp41 HIV-2 Rod which consists of 239 amino acids of the CKS protein, followed by 18 amino acids from the pTB21-multiple restriction site linker (non-HIV amino acids), 108 amino acids from the HIV-2 env protein (p41 Rod) and an additional 10 amino acids from the pTB210 multiple restriction site linker (non-HIV amino acids).

The plasmid pJC100 was transformed into *E. coli* K-12 strain XL-1 (recA1, endA1, gyrA96, Thi-1, hsdR17, supE44, relA1, Lac-/F', proAB, lacIqZdeltaM15, TN10) cells made competent by the well-known calcium chloride method. In this construction, the expression of the rp41 HIV-2 Rod fusion protein was under the control of the lac promoter. The antigen was induced by the addition of isopropyl thiogalactose (IPTG). The plasmid replicated as an independent element, was non-mobilizable and was and is maintained at approximately 10 to 30 copies per cell.

An isolated colony of pJC100/XL-1 was grown overnight at 37° C. in media consisting of tryptone, yeast extract, glucose, phosphate salts and ampicillin. This culture was brought to 15% glycerol, aliquoted in 1 ml portions and frozen at −70° C. This cell bank served as the source of immunogen used for the subsequent mouse immunizations.

An aliquot of the cell bank was used to inoculate 1.6L of the above growth medium and grown at 37° C. with shaking to an optical density (600 nm) of 0.5 when antigen expression was induced by the addition of IPTG. Three hours post induction the biomass was separated from the media and stored frozen at −20° C. until mice were immunized.

B. Immunization of Mice

The immunization regimen (10 mice) consisted of the primary immunization with additional immunizations on days 14 and 29. For each immunization, 10 μg of 0.1% sodium dodecyl sulfate (SDS) solubilized pJC100/XL-1 prepared as described above was emulsified with RIBI adjuvant. This emulsified immunogen was inoculated intraperitoneally and subcutaneously. Individual mice were screened for microtiter plate enzume immunoassay (EIA) immunoreactivity by standard well-known methods with the immunogen approximately four weeks after the third immunization. Fifteen weeks after the third immunization mice were inoculated intraveneously with 10 μg of immunogen.

C. Establishment of Myeloma Cell Line

Three days after the intravenous boost, splenocytes were fused with Sp2/0-Ag14 myeloma cells obtained from Milstein Laboratories, England, using the polyethylene glycol (PEG) method. The fusions were cultured in Iscove's Modifid Dulbecco's Medium (IMDM) containing 10% fetal calf serum (FCS), plus 1% hypoxanthine, aminopterin and thymidine (HAT). Bulk cultures were screened by microtiter plate EIA using the immunogen as described in part (B) above solubilized in 6M guanidine HCl. Reactive cultures were subcloned and screened with purified rp41 HIV-2 Rod from pJC100/XL-1 (immunogen) and rp41 HIV-2 ("Diagen", disclosed in EPO Publ. No. 0370458, incorporated herein by reference), and recombinant HIV-2 p41 antigen pJC104/XL-1 (Diagen strain). Both HIV-2 antigens were purified from lysozome treated sonicated biomass. The lysates were clarified by centrifugation and the insoluble fractions recovered. The pellets were washed sequentially with 5% Triton X-100® (available from Sigma Chemical Co., St. Louis, Mo.), 1% sodium deoxycholate and Tris-EDTA buffer. The washed pellets, solubilized and clarified in 6M guanidine HCl, were used to coat microtiter plates for this process. Briefly, 100 μg/ml of a one μg/ml solution/well was incubated overnight at room temperature. CKS purified from the expression vector (pTB210/XL-1 as formulated in the specimen diluent of the Abbott HIVAB® HIV-1/HIV-2 EIA) (available from Abbott Laboratories, Abbott Park, IL) was used in the screening microtiter plate format to identify and eliminate monoclonal antibody secreting clones reactive with the CKS component of the fusion protein. Thus, the clones selected for final expansion were reactive with the gp41 component of both recombinant rp41 proteins. One such clone, designated as 7-1054-180, was selected for further study. Clone 7-1054-180 culture was expanded, aliquoted and frozen in IMDM containing 10% FCS and 10% dimethylsulfoxide.

EXAMPLE 2

Production and Purification of 7-1054-180 Monoclonal Antibody

The following procedures were used in the production and purification of monoclonal antibody 7-1054-180.

A. Production of Ascites Fluid Containing the 7-1054-180 Monoclonal Antibody

Ampules of frozen 7-1054-180 hybridoma cells from the cell bank were thawed and placed into expansion culture. Viable hydridoma cells were inoculated intraperitoneally into Pristane treated mice. Ascitic fluid was removed from the mice, pooled, filtered through a 0.2μ filter and subjected to an immunoglobulin class G (IgG) analysis to determine the volume of the Protein A column required for the purification.

B. Purification of Monoclonal Antibody 7-1054-180 From Ascites Fluid

Briefly, filtered and thawed ascites fluid was mixed with an equal volume of Protein A sepharose binding buffer (1.5M glycine, 3.0M NaCl, pH 8.9) and refiltered through a 0.2μ filter. The volume of the Protein A column was determined by the quantity of IgG present in the ascites. The ascites then was applied to the Protein A chromatography column (available from Pharmacia, Piscataway, N.J.), and the column was washed with the above binding buffer. Washing was continued until a stable absorbance (280 nm) baseline was obtained. The antibody was eluted from the Protein A column with 0.1M citric acid, pH 4.5. The eluate then was dialyzed against PBS overnight at 2-8° C. The dialyzed 7-1054-180 IgG was sterile filtered and dispensed in aliquots, and stored at −80° C.

EXAMPLE 3

Characterization of HIV-2 Reactive Monoclonal Antibody

Biochemical and immunological characterization was performed on monoclonal antibody 7-1054-180 as follows.

A. Antigen characterization

The following criteria were examined for characterization of the monoclonal antibody: physical appearance, final pH, microbial load, antibody potency, SDS-PAGE electrophoresis, chromatography, immunological reactivity and specific activity. The following data was noted about the monoclonal antibody 7-1054-180 as determined by analysis of three separate lots.

The physical appearance of the monoclonal antibody by visual inspection appeared as a colorless and clear liquid at ambient temperature. The final pH of the monoclonal antibody, measured by using standard laboratory techniques, was 7.1 for two lots, and 7.2 for one lot, of the monoclonal antibody. Microbial load analysis was performed on each lot of monoclonal antibody. Following filtration of the monoclonal antibody through a 0.45μ filter, the filter was incubated at 32° C. on trypticase soy agar for three days. The filter was examined for bacterial growth at the end of the incubation period. No microbial growth was detected following the incubation of the 0.45μ filter on trypticase soy agar after three days incubation at 32° C.

Antibody potency was based on protein content determined by quantitative amino acid analysis. Antibody samples were vacuum desiccated and subjected to vapor hydrolysis with 6N HCl and 1% phenol at 150° C. for two hours. Derivatization was done using a modified Millipore-Waters phenylthiocarbamyl (PTC) protocol. Samples were analyzed in triplicate with alpha amino-n-butyric acid as an internal standard, on a Waters HPLC equipped with a Maxima 820 Data System. The protein concentration was calculated from quantitative amino acid composition to be 1.14 mg/ml for lot 1, 4.48 mg/ml for lot 2, and 2.17 mg/ml for lot 3. The data obtained from the quantitative amino acid analyses were used to determine the molar ratio of amino acid residues for the three lots of monoclonal antibody tested. Cysteine and tryptophan were not included in these analyses because it has been found that they are partially or totally destroyed during hydrolysis. The actual amino acid composition data for the monoclonal antibody 7-1054-180 is shown in Table 1. The experimentally determined molar ratio for each of the 16 amino acids was reproducible among the three lots and had an overall percent coefficient of variation (% CV) of 4.4%.

Figure 3A:
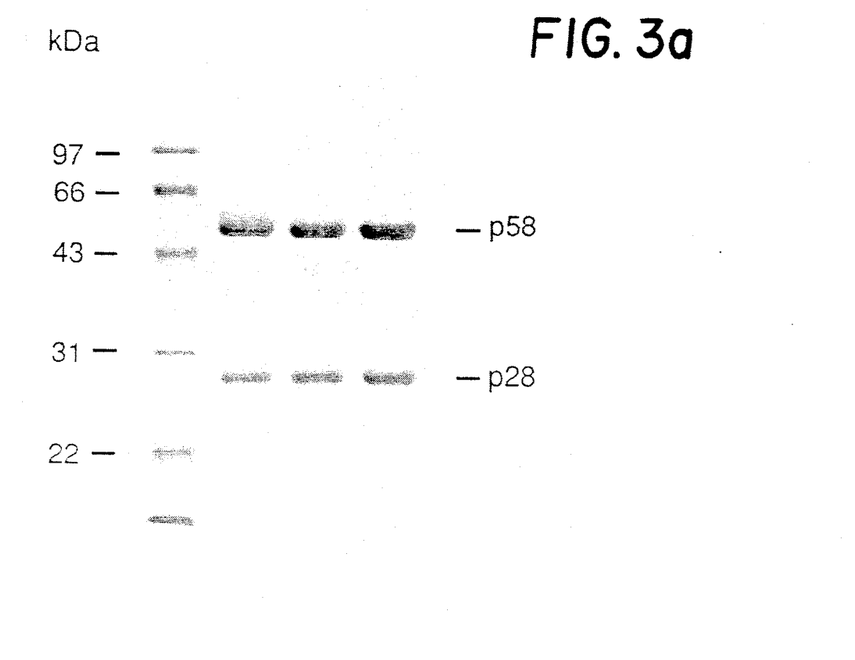
FIG. 3 presents the results of staining with (A) Coomassie Brilliant Blue R-25 and (B) silver-stained SDS-PAGE gels, and monoclonal antibody 7-1054-180
Figure 3B:
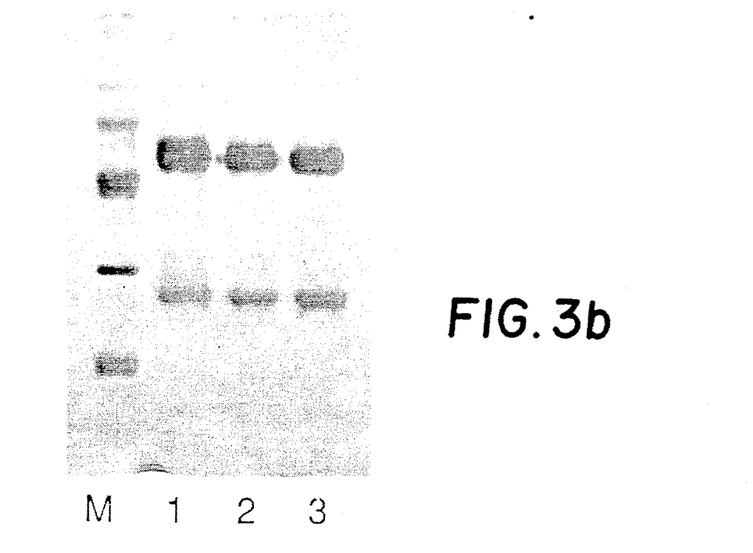

Antibody lots were analyzed for identity using polyacrylamide gel electrophoresis in the presence of SDS (SDS-PAGE) using reducing conditions. Gels were stained with Coomassie Brilliant Blue R-250 following methods available to the routineer. The presence of proteins at the correct molecular size for IgG heavy and light chains was confirmed. Scanning densitometry was performed on Coomassie stained gels to evaluate purity. The quantity of protein on the scanned gel was in the linear range of Coomassie binding. Electrophoresis of each SDS-PAGE gel was stopped before the dye front migrated off the gel. The results of staining with Coomassie Brilliant Blue R-25 are presented in FIG. 3(A). Two bands corresponding to IgG heavy chain (58,000 Daltons, Da) and IgG light chain (28,000 Da) were observed. Silver-stained SDS-PAGE gels prepared by methods known to those of skilled in the art which contained the same quantity of protein as was loaded on the Coomassie stained gel demonstrated that the qualitative presence of assorted impurities was constant but quantitative variations were detected. Results of the silver stained SDS-PAGE gels are presented in FIG. 3 (B). Lot 1, in lane 1, was slightly less pure than the other two lots, when equal quantities of each lot of monoclonal antibody were applied to the gel.

Scanning densitometry of the Coomassie stained gel was used to quantitate the percentages of the major components present in the monoclonal antibody lots. The results showed a calculated average purity for the 58,000 Da band plus the 28,000 Da band to be greater than 95% of the total Coomassie stainable material for all three lots of the monoclonal antibody. As from the Coomassie stained and silver stained gel, lot 1 showed slightly less purity than the other lots, but the calculated purity still was in excess of 95%.

Lots 1, 2 and 3 of monoclonal antibody were chromatographed using a Bio Rad Sio-Sil SEC-400 gel permeation column in phosphate buffered saline (PBS), pH 7.2. The molecular size was determined and the method used to assess relative purity and structural integrity. Ten (10) μg samples of monoclonal antibody were analyzed using a Bio-Rad SEC-400 column (Bio-Rad, Richmond, Calif.) in PBS at a flow rate of 1 ml/min. The profiles were consistent for each of the three lots tested. The molecular size was comparable to an IgG standard chromatographed under the same conditions; peak retention times were 8.90 min for lot 1, 8.95 min for lot 2, 8.95 min for lot 3 and 8.90 min for the IgG standard. The area under the peak was >95% of the total 280 nm absorbance detected in each chromatography. Neither aggregation nor obvious degradation was detected in any lot of the monoclonal antibody.

Figure 4:
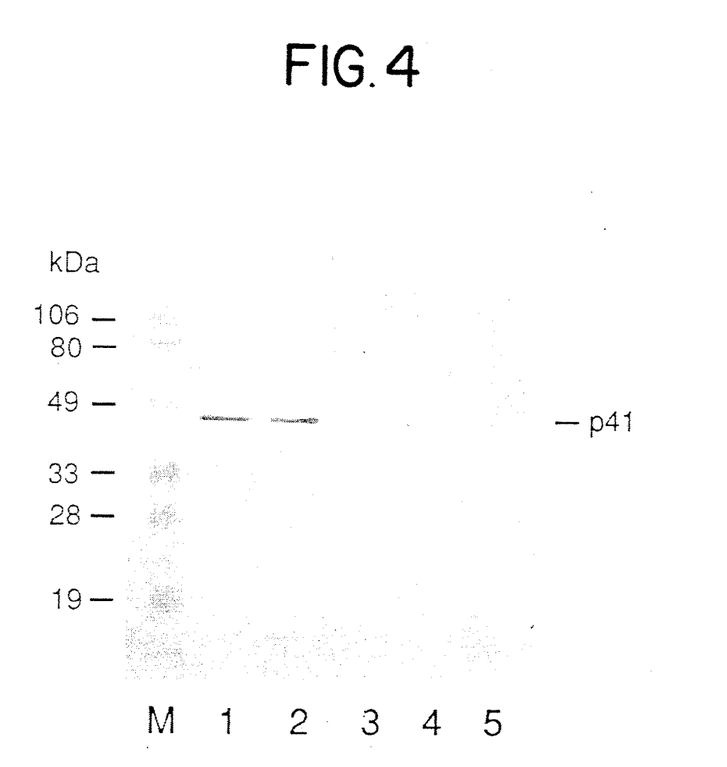
FIG. 4 presents the results of the reactivity of a representative lot of monoclonal antibody 7-1054-180 with recombinant HIV-2 and HIV-1 antigens for lot 1.
Figure 5A:
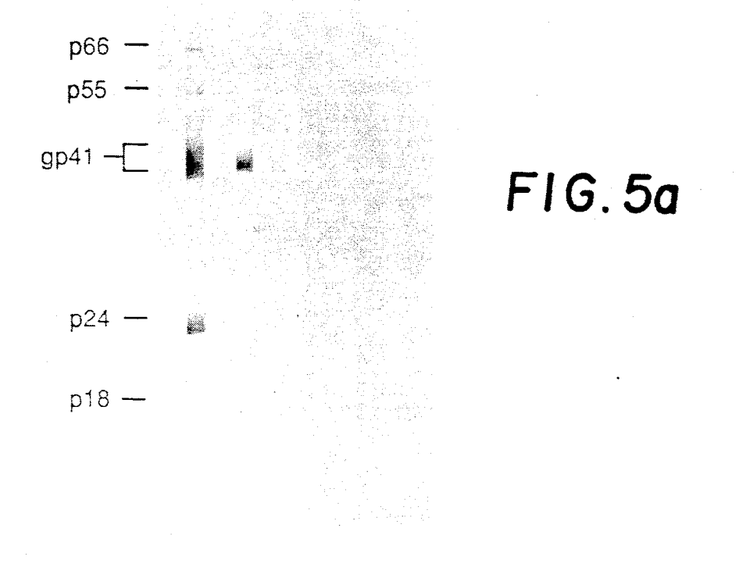
FIGS. 5A and 5B presents the reactivities of lots 1, 2 and 3 of monoclonal antibody 7-1054-180 with HIV-1 viral protein (FIG. 5A) and HIV-2 viral proteins (FIG. 5B) immobilized on conventional immunoblot strips.

The immunological reactivity of each lot of monoclonal antibody 7-1054-180 for the immunogen, recombinant HIV-2 and recombinant HIV-1 antigens, purified CKS and an *E. coli* lysate was determined by immunoblot. Each lot of HIV-2 monoclonal antibody 7-1054-180 was used as primary antibody probe to examine its reactivity with the various proteins. Lane M in FIG. 5 contains molecular weight standards at 19 kilodaltons (kDa), 28 kDa, 33 kDa, 49 kDa, 80 kDa and 106 kDa. The reactivities of each lot of monoclonal antibody with recombinant HIV-2 and HIV-1 antigens were determined. The results for a representative lot are presented in FIG. 4. For all three lots, immunoblot activity was detected with the immunogen rp41 HIV-2 Rod (Lane 1) and rp HIV-2 Diagen (Lane 2). No lot of monoclonal antibody reacted with HIV-1 rpCKS-41 (recombinant HIV-1 antigen from pTB319/XL-1 cells, Lane 3), recombinant CKS (Lane 4) or a lysate of *E. coli* cells (Lane 5). The blot reactivities with recombinant HIV-2 antigens were consistent qualitatively for all lots of monoclonal antibody.

Figure 5B:
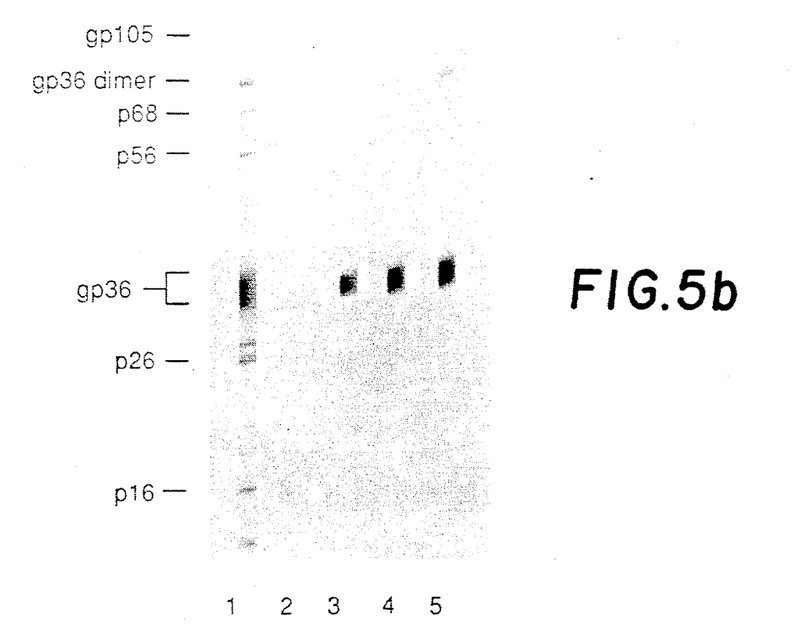

The reactivities of each lot of monoclonal antibody with HIV-1 and HIV-2 viral proteins immobilized on conventional immunoblot strips is shown in FIG. 5A and FIG. 5B. A nitrocellulose immunoblot strip containing HIV-1 viral proteins (IIIB isolate, FIG. 5A) was reacted with an HIV-1 positive human serum using the standard goat anti-human conjugate (available from Bio-Rad, Richmond, Calif.) which showed the full spectrum of reactivity (Lane 1). The strip in Lane 2 was reacted with a murine antibody specific to HIV-1 gp41, followed by a goat anti-mouse conjugate. The observed reactivity showed that the conventional immunoblot strips could be used effectively for this analysis. The HIV-1 strips in Lanes 3, 4 and 5 were reacted with each lot of the 7-1054-180 monoclonal antibody and this was followed by reaction with a goat-anti mouse conjugate (available from Bio-Rad, Richmond, Calif.). As can be discerned from FIG. 5A, the monoclonal antibody 7-1054-180 did not react with any HIV-1 protein.

A nitrocellulose immunoblot strip containing HIV-2 viral protein (Barin isolate) was tested similarly. The results are shown in FIG. 5B. Lane 1 shows a positive human serum which was reactive with HIV-2 proteins. Lane 2 contained a murine antibody specific to HIV-1 gp41, and the lack of reactivity as seen in Lane 2 of FIG. 5B is believed due to the lack of cross-reactivity between the HIV-1 monoclonal antibody used and HIV-2 proteins. Lanes 3, 4, and 5 contained the reaction of lots 1, 2 and 3, respectively, of the 7-1054-180 monoclonal antibody followed by reaction with a goat anti-mouse conjugate (available from Bio-Rad, Richmond, Calif.). The reactivity of the 7-1054-180 monoclonal antibody with HIV-2 gp36 monomer and gp36 oligomer shown with these lots of the 7-1054-180 monoclonal antibody further illustrates specific reactivity with HIV-2 (Pau et al., *Lancet* 337:616-617 (1991).

When the data from FIG. 5A and FIG. 5B are taken together, the results of the recombinant and native immunoblot analyses showed that the three lots of 7-1054-180 were reactive with epitopes present on HIV-2 gp41 and not present on HIV-1 gp41. We are in the process of mapping the epitope specifically bound by the 7-12054-180 monoclonal antibody. Although the epitope specificity of the 7-1054-180 monoclonal antibody has not been conclusively mapped, type-specific reactivities on the transmembrane glycoprotein of HIV-2 have been mapped. See Gnan et al., *Science* 237:1346-1349 (1987).

The specific activity was determined by diluting each lot of 7-1054-180 monoclonal antibody and testing each dilution in an EIA test to determine the antibody protein in 0.15 ml required to produce an optical density (OD) of 0.7 in the assay format. It was determined from dilution curves of each lot of the monoclonal antibody that this amount ranged from 0.72 μg to 0.81 μg. The % CV for this testing was 5.9%.

The isotype and IgG subtype of the 7-1054-180 monoclonal antibody were determined for each lot of monoclonal antibody using an Amersham murine antibody EIA typing kit (available from Amersham, Inc. Arlington Heights, Ill.). The predominant subtype, based on dilution,for each lot of antibody was IgG subtype 1 (kappa chain). This was further confirmed by a subtyping analysis on IgG isolated from cellculture fluid from the 7-1054-180 hybridoma.

EXAMPLE 3

Stability Testing of the 7-1054-180 Monoclonal Antibody

The stability of a lot of the 7-1054-180 monoclonal antibody was performed by placing an aliquot of the monoclonal antibody and a dilution of an HIV-2 positive sample in storage at 2°-8° C. for continuous storage, and assaying for OD readings throughout the study. The assays were performed at 0 days, 7 days, 1 month, 3 months, 4 months, 5 months, 6 months, 8 months 11 days and 11 months 7 days in this study. The OD of the monoclonal antibody showed minimal decline in signal throughout the study. It also was determined that the 7-1054-180 monoclonal antibody was comparable in stability to the diluted HIV-2 positive serum sample.

EXAMPLE 4

Use of 7-1054-180 Monoclonal Antibody as a Positive Control

Monoclonal antibody 7-1054-180 was used as a positive control in an assay which determines the presence of either HIV-1 or HIV-2, or both, in test samples. In this procedure, recombinant p24 (HIV-1 gag)., gp41 (HIV-1 env) and gp41 (HIV-2 env, Diagen clone) were immobilized on a polystyrene bead. The bead then was contacted with the 7-1054-180 monoclonal antibody and incubated. HIV antibodies were detected by the addition of HIV-1 gag and env and HIV-2 env recombinant antigens labeled with horseradish peroxidase (HRPO). These assays were performed during two separate testing periods at five different test sites (Community Blood Center of Greater Kansas City, Kansas City, Mo., North American Biologicals, Inc., Miami, Fla., Louisana Blood Center, Shreveport La., Blood Systems Central Lab, Scottsdale, Ariz., and Abbott Laboratories, Abbott Park, Ill.). The data are presented in Tables 1 and 2.

TABLE 2

| Total | Overall Reproducibility of 7-1054-180 Results | | | | | | |
|---|---|---|---|---|---|---|---|
|  | Mean | Intra-Assay | | Inter-Assay | | Between Site | |
| (n) | S/CO | SD | CV | SD | CV | SD | CV |
| 72 | 5.289 | 0.4341 | 8.2 | 0.4367 | 8.3 | 0.5059 | 9.6 |

TABLE 3

| Total | Overall Reproducibility of 7-1054-180 Results | | | | | | |
|---|---|---|---|---|---|---|---|
|  | Mean | Intra-Assay | | Inter-Assay | | Between Site | |
| (n) | S/CO | SD | CV | SD | CV | SD | CV |
| 72 | 7.861 | 0.6853 | 8.7 | 0.7496 | 9.5 | 0.8304 | 10.6 |

The 7-1054-180 cell line which produces the monoclonal antibody 7-1054-180 was deposited under the terms of the Budapest Treaty at the American Type Culure Collection, 12301 Parklawn Drive, Rockville, Md., 20852, as of Nov. 1, 1991, under A.T.C.C. Deposit No. HB 10908.

The monoclonal antibody of the invention can be used in a variety of ways, including its use as a capture agent or as part of an indicator reagent in various assay formats, as a positive control for diagnostic or research tests, as a tool for purification. Other uses and variations of the invention disclosed herein will be apparent to those skilled in the art.

TABLE I

| AMINO ACID COMPOSITION BY % WEIGHT RATIOS THREE LOTS OF MAb anti-HIV-2 | | | |
|---|---|---|---|
| AMINO ACID RESIDUE | EXPERIMENTAL % WEIGHT RATIOS | | |
|  | LOT 1 | LOT 2 | LOT 3 |
| ASX | 9.1 | 8.4 | 8.6 |
| GLX | 11.3 | 11.3 | 11.9 |
| SER | 8.2 | 8.1 | 8.7 |
| GLY | 3.6 | 6.7 | 4.7 |
| HIS | 2.5 | 2.5 | 2.6 |
| ARG | 4.9 | 4.2 | 4.7 |
| THR | 9.1 | 8.7 | 9.5 |
| ALA | 3.7 | 3.6 | 3.9 |
| PRO | 6.8 | 6.5 | 7.1 |
| TYR | 6.0 | 5.7 | 6.1 |
| VAL | 7.8 | 7.6 | 8.2 |
| MET | 2.0 | 1.8 | 1.8 |
| ILE | 4.3 | 4.2 | 4.6 |
| LEU | 7.4 | 7.2 | 7.7 |
| PHE | 5.2 | 5.2 | 5.7 |
| LYS | 8.2 | 8.2 | 8.5 |

What is claimed is:

1. A monoclonal antibody that specifically binds to HIV-2 gp36 antigen and does not bind to HIV-1 antigens, which is secreted by the cell line A.T.C.C. Deposit No. HB 10908.

2. A hybridoma cell line which secretes a monoclonal antibody which specifically binds to HIV-2 gp36 antigen and does not specifically bind to HIV-1 antigens, wherein the cell line is A.T.C.C Deposit No. HB 10908.

* * * * *